(12) United States Patent
Johnston et al.

(10) Patent No.: US 8,923,979 B1
(45) Date of Patent: Dec. 30, 2014

(54) SYSTEMS AND METHODS FOR PROVIDING A PRE-STIMULATION VISUAL CUE REPRESENTATIVE OF A COCHLEAR IMPLANT STIMULATION LEVEL

(71) Applicant: Advanced Bionics AG, Staefa (CH)

(72) Inventors: Jacob Johnston, Moorpark, CA (US); Guillermo A. Calle, Moorpark, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/214,012

(22) Filed: Mar. 14, 2014

Related U.S. Application Data

(62) Division of application No. 12/847,193, filed on Jul. 30, 2010, now Pat. No. 8,700,168.

(51) Int. Cl.
*A61N 1/36* (2006.01)
*A61N 1/18* (2006.01)

(52) U.S. Cl.
CPC .................................. *A61N 1/36032* (2013.01)
USPC ............................................. 607/57; 607/137

(58) Field of Classification Search
None
See application file for complete search history.

(56) References Cited

U.S. PATENT DOCUMENTS

| 7,043,303 | B1 | 5/2006 | Overstreet |
| 2008/0174570 | A1 | 7/2008 | Jobs et al. |
| 2008/0221637 | A1 | 9/2008 | Woods et al. |
| 2008/0288023 | A1 | 11/2008 | John |
| 2009/0018616 | A1 | 1/2009 | Quick et al. |
| 2009/0138061 | A1 | 5/2009 | Stephens et al. |

OTHER PUBLICATIONS

Non-Final Office Action received in U.S. Appl. No. 12/847,193, dated May 30, 2013.
Final Office Action received in U.S. Appl. No. 12/847,193, dated Jul. 17, 2013.
Non-Final Office Action received in U.S. Appl. No. 12/847,193, dated Aug. 29, 2013.

*Primary Examiner* — Brian T Gedeon
*Assistant Examiner* — Ankit Tejani
(74) *Attorney, Agent, or Firm* — ALG Intellectual Property, LLC

(57) ABSTRACT

An exemplary system includes at least one computing device communicatively coupled to a cochlear implant system and that 1) determines one or more control parameters to be used by the cochlear implant system to apply electrical stimulation to a patient, 2) determines, based on the one or more control parameters, a target stimulation level to be used by the cochlear implant system to apply the electrical stimulation to the patient, and 3) displays a pre-stimulation visual cue indicative of the determined target stimulation level in a graphical user interface prior to the cochlear implant system using the one or more control parameters to apply the electrical stimulation to the patient. Corresponding systems and methods are also described.

20 Claims, 10 Drawing Sheets

SYSTEMS AND METHODS FOR PROVIDING A PRE-STIMULATION VISUAL CUE REPRESENTATIVE OF A COCHLEAR IMPLANT STIMULATION LEVEL

RELATED APPLICATIONS

The present application is a divisional application of U.S. patent application Ser. No. 12/847,193, filed Jul. 30, 2010, which is incorporated herein by reference in its entirety.

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

When an implantable cochlear device of a cochlear implant system is initially implanted in a patient, and during follow-up tests and checkups thereafter, it is usually necessary to fit the cochlear implant system to the patient. Fitting of a cochlear implant system to a patient is not an exact science but an ongoing trial-and-error-based iterative exercise that is largely dependent on the experience of and feedback provided by the patient. For example, in a fitting session, an audiologist or the like typically utilizes a fitting system to present various stimuli to the patient and relies on subjective feedback from the patient as to how such stimuli are perceived. Based on this process, the audiologist utilizes the fitting system to configure the cochlear implant system for operation.

A significant part of fitting the cochlear implant system to the patient includes measurement of phsycophysically-determined comfort threshold levels. For each stimulation channel of the cochlear implant system, a minimum threshold level is measured. The minimum threshold level, which is typically referred to as a "T" level, generally represents the minimum stimulation level which, when applied to a given electrode associated with the channel, produces a sensed perception of sound by the patient at least fifty percent of the time. Similarly, for each stimulation channel of the cochlear implant system, a most-comfortable threshold level is measured. The most-comfortable level, which is typically referred to as an "M" level, represents a stimulation level which, when applied to the given electrode associated with the channel, produces a sensed perception of sound by the patient that is moderately loud, or comfortably loud, but not so loud that the perceived sound is uncomfortable. Once measured, these "T" and "M" levels may be used by the fitting system in order to properly map sensed sound to stimulation levels that can be perceived by the patient as sound.

Measurement of the "T" and/or "M" levels (or other thresholds) associated with each channel of a multichannel cochlear implant system is an extremely laborious and time-intensive task. Such determinations require significant time commitments on the part of the audiologist, as well as the patient. To assist the audiologist with the measurement of the "T" and/or "M" levels (or other thresholds), the fitting subsystem typically provides a graphical user interface including an abundance of information and tools that may be used by the audiologist. For example, the graphical user interface may include multiple markers, adjustors, or other user-controllable tools that may be used by the audiologist to adjust settings such as "T" and/or "M" levels for a fitting session. In addition, during a fitting session, the fitting system may operate in a number of different operational modes that cause different and varying electrical stimulation to be applied using varying stimulation channels. Because of the amount of information and number of user-controllable tools provided in the graphical user interface, as well as the different operational modes of the fitting system, the audiologist may not always be able to readily and intuitively know precisely what stimulation levels will be used to apply electrical stimulation to a patient before the stimulation is actually applied.

SUMMARY

An exemplary method of providing a pre-stimulation visual cue representative of a cochlear implant stimulation level includes a fitting subsystem 1) determining one or more control parameters to be used by a cochlear implant system to apply electrical stimulation to a patient, 2) determining, based on the one or more control parameters, a target stimulation level to be used by the cochlear implant system to apply the electrical stimulation to the patient, and 3) displaying a pre-stimulation visual cue indicative of the determined target stimulation level in a graphical user interface prior to the cochlear implant system using the one or more control parameters to apply the electrical stimulation to the patient.

Another exemplary method of providing a pre-stimulation visual cue representative of a cochlear implant stimulation level includes a fitting subsystem 1) determining, by a fitting subsystem based on one or more control parameters, a target stimulation level to be used by a cochlear implant system communicatively coupled to the fitting subsystem to apply electrical stimulation to a patient in accordance with a cochlear implant fitting procedure, and 2) displaying, by the fitting subsystem, a pre-stimulation visual cue indicative of the determined target stimulation level in a stimulation chart in a graphical user interface prior to the cochlear implant system using the one or more control parameters to apply the electrical stimulation to the patient in accordance with the cochlear implant fitting procedure.

An exemplary system of providing a pre-stimulation visual cue representative of a cochlear implant stimulation level includes 1) a communication facility communicatively coupled to a cochlear implant system, 2) a fitting facility communicatively coupled to the communication facility and configured to direct the cochlear implant system to apply electrical stimulation to a patient in accordance with a cochlear implant fitting procedure, 3) a pre-stimulation facility communicatively coupled to at least one of the communication facility and the fitting facility and configured to determine one or more control parameters to be used by the cochlear implant system to apply the electrical stimulation to the patient in accordance with the cochlear implant fitting procedure and to determine a target stimulation level based on the one or more control parameters, and 4) a user interface facility communicatively coupled to the pre-stimulation facility and configured to display a pre-stimulation visual cue indicative of the determined target stimulation level in a graphical user interface prior to the fitting facility directing the cochlear implant system to apply the electrical stimulation to the patient in accordance with the cochlear implant fitting procedure.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Methods and systems for providing a pre-stimulation visual cue representative of a cochlear implant stimulation level are described herein. As described in more detail below, a fitting subsystem may be configured to determine one or more control parameters to be used by a communicatively coupled cochlear implant system to apply electrical stimulation to a patient, determine, based on the one or more control parameters, a target stimulation level to be used by the cochlear implant system to apply the electrical stimulation to the patient, and display a pre-stimulation visual cue indicative of the determined target stimulation level in a graphical user interface ("GUI") prior to the cochlear implant system using the one or more control parameters to apply the electrical stimulation to the patient.

Numerous advantages may be associated with the methods and systems described herein. For example, by determining a target stimulation level and displaying a pre-stimulation visual cue indicative of the determined target stimulation level in a GUI prior to application of electrical stimulation to a cochlear implant patient, the fitting subsystem may assist an audiologist or the like in intuitively, conveniently, and/or efficiently ascertaining the target stimulation level before electrical stimulation is actually applied to the patient. Accordingly, the pre-stimulation visual cue may assist the audiologist in understanding information presented in the GUI and in avoiding use of unexpected stimulation levels in actual applications of electrical stimulation.

Figure 1:
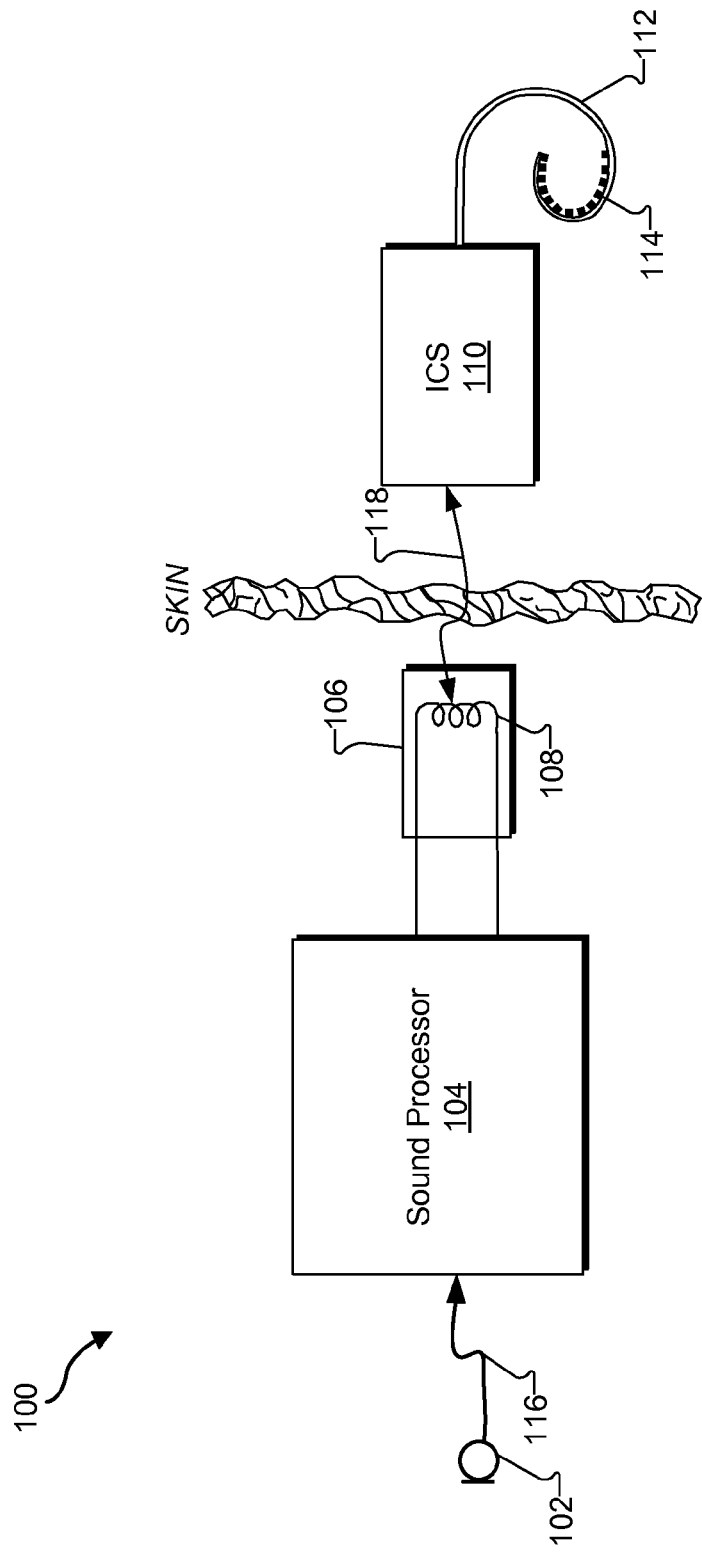
FIG. 1 illustrates an exemplary cochlear implant system according to principles described herein.

To facilitate an understanding of the methods and systems described herein, an exemplary cochlear implant system 100 will be described in connection with FIG. 1. As shown in FIG. 1, cochlear implant system 100 may include a microphone 102, a sound processor 104, a headpiece 106 having a coil 108 disposed therein, an implantable cochlear stimulator ("ICS") 110, and a lead 112 with a plurality of electrodes 114 disposed thereon. Additional or alternative components may be included within cochlear implant system 100 as may serve a particular implementation.

As shown in FIG. 1, microphone 102, sound processor 104, and headpiece 106 may be located external to a cochlear implant patient, and implantable cochlear stimulator 110, lead 112, electrodes 114 may be implanted subcutaneously with the patient. In some alternative examples, microphone 102 and/or sound processor 104 may also be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct implantable cochlear stimulator 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing program loaded on sound processor 104 to generate appropriate stimulation parameters for controlling implantable cochlear stimulator 110. In certain examples, sound processor may 104 may include multiple sound processing programs loaded thereon such that a patient may select, from the multiple sound processing programs, which sound processing program to utilize to generate stimulation parameters. Accordingly, the patient may select a sound processing program that is well suited for a particular situation.

Sound processor 104 may include or be implemented by a behind-the-ear ("BTE") unit, a portable speech processor ("PSP"), and/or any other sound processing unit as may serve a particular implementation. Exemplary components of sound processor 104 will be described in more detail below.

Sound processor 104 may be configured to transcutaneously transmit one or more control parameters and/or one or more power signals to implantable cochlear stimulator 110 with coil 108 by way of a communication link 118. These control parameters may be configured to specify one or more stimulation parameters, operating parameters, and/or any other parameter by which implantable cochlear stimulator 110 is to operate as may serve a particular implementation. Exemplary control parameters include, but are not limited to, stimulation current levels, volume control parameters, program selection parameters, operational state parameters (e.g., parameters that turn a sound processor and/or an implantable cochlear stimulator on or off), audio input source selection parameters, fitting parameters, noise reduction parameters, microphone sensitivity parameters, microphone direction parameters, pitch parameters, timbre parameters, sound quality parameters, most comfortable current levels ("M" levels), threshold current levels ("T" levels), clipping levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within implantable cochlear stimulator 110. In this manner, control parameters and power signals may be wirelessly transmitted between sound processor 104 and implantable cochlear stimulator 110 via communication link 118. It will be understood that data communication link 118 may include a bi-directional communication link and/or one or more dedicated uni-directional communication links. In some alternative embodiments, sound processor 104 and implantable cochlear stimulator 110 may be directly connected with one or more wires or the like.

Implantable cochlear stimulator 110 may be configured to generate electrical stimulation representative of an audio signal detected by microphone 102 in accordance with one or more stimulation parameters transmitted thereto by sound processor 104, which stimulation parameters may be generated by sound processor 104 in accordance with a sound processing program loaded on the sound processor 104. Implantable cochlear stimulator 110 may be further configured to apply the electrical stimulation received from sound processor 104 to one or more stimulation sites within the cochlea via one or more electrodes 114 disposed along lead 112. In some examples, implantable cochlear stimulator 110 may include a plurality of independent current sources each associated with a stimulation channel defined by one or more of electrodes 114. In this manner, different stimulation current levels may be applied to multiple stimulation sites simultaneously by way of multiple electrodes 114. In such examples, cochlear implant system 100 may be referred to as a "multi-channel cochlear implant system."

To facilitate application of the electrical stimulation generated by implantable cochlear stimulator 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
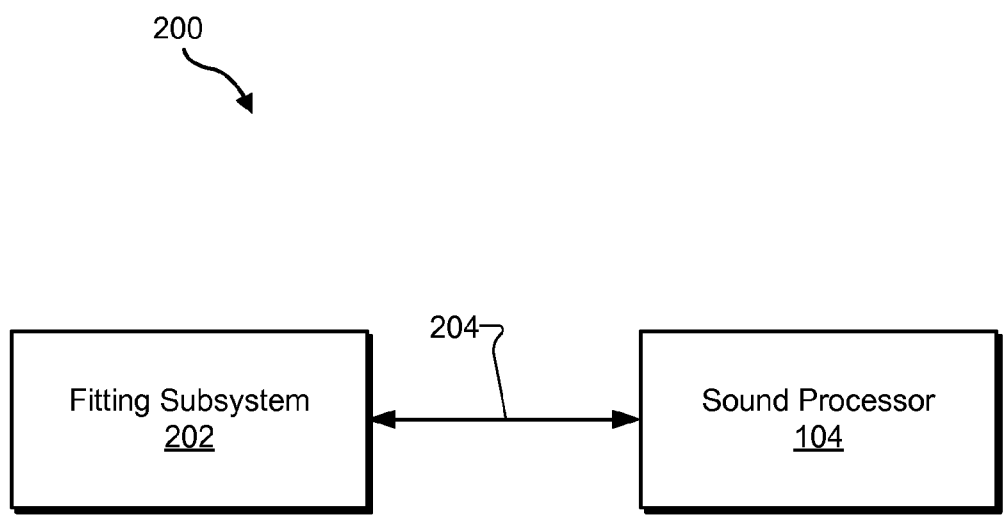
FIG. 2 illustrates an exemplary cochlear implant fitting system according to principles described herein.

FIG. 2 illustrates an exemplary cochlear implant fitting system 200 (or simply "fitting system 200") that may be used to fit cochlear implant system 100 to a patient. A fitting may include performance of one or more procedures by fitting system 200 to fit sound processor 104 to the patient. As used herein, the terms "fitting a sound processor to a patient" and "fitting a cochlear implant system to a patient" will be used interchangeably to refer to performing one or more fitting procedures associated with sound processor 104 and/or any other component of cochlear implant system 100. Such fitting procedures may include, but are not limited to, adjusting one or more control parameters by which sound processor 104 and/or implantable cochlear stimulator 110 operate, measuring one or more electrode impedances, performing one or more neural response detection operations, performing one or more testing, diagnostic, and/or troubleshooting operations associated with the cochlear implant system, and performing one or more fitting operations in accordance with one or more operational modes of fitting system 100. As described further below, in certain examples, one or more fitting operations of a fitting procedure may be performed by fitting system 100 such that cochlear implant system 100 applies electrical stimulation to a patient in accordance with one or more target stimulation levels and/or the fitting procedure.

As shown in FIG. 2, fitting system 200 may include a fitting subsystem 202 configured to be selectively and communicatively coupled to sound processor 104 of cochlear implant system 100 by way of a communication link 204. Fitting subsystem 202 and sound processor 104 may communicate using any suitable communication technologies, devices, networks, media, and protocols supportive of data communications.

Fitting subsystem 202 may be configured to perform one or more of the fitting procedures and/or operations described herein. To this end, fitting subsystem 202 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation.

Figure 3:
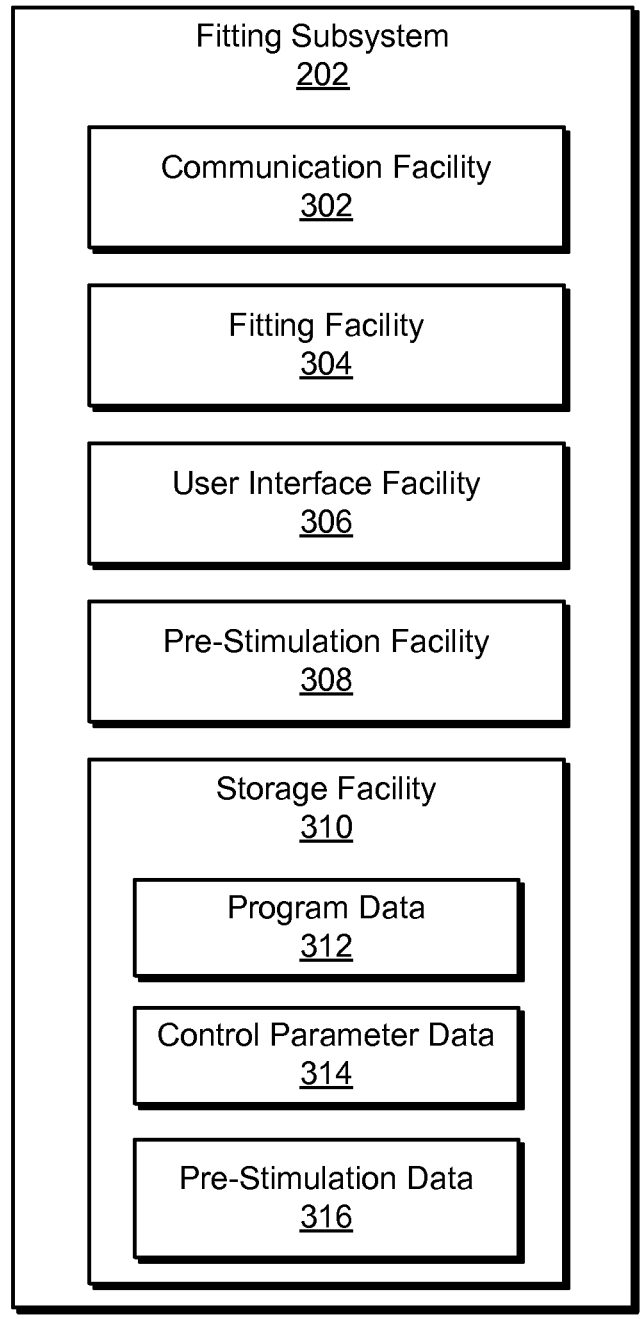
FIG. 3 illustrates exemplary components of an exemplary fitting subsystem according to principles described herein.

FIG. 3 illustrates exemplary components of fitting subsystem 202. As shown in FIG. 3, fitting subsystem 202 may include a communication facility 302, a fitting facility 304, a user interface facility 306, a pre-stimulation facility 308, and a storage facility 310, which may be communicatively coupled to one another using any suitable communication technologies. Each of these facilities will now be described in more detail.

Communication facility 302 may be configured to facilitate communication between fitting subsystem 202 and sound processor 104. For example, communication facility 302 may be implemented by a CPI device, which may include any suitable combination of components configured to allow fitting subsystem 202 to interface and communicate with sound processor 104. Communication facility 302 may additionally or alternatively include one or more transceiver components configured to wirelessly transmit data (e.g., program data and/or control parameter data) to sound processor 104 and/or wirelessly receive data (e.g., feedback data, impedance measurement data, neural response data, etc.) from sound processor 104.

Communication facility 302 may additionally or alternatively be configured to facilitate communication between fitting subsystem 302 and one or more other devices. For example, communication facility 302 may be configured to facilitate communication between fitting subsystem 202 and one or more computing devices (e.g., by way of the Internet and/or one or more other types of networks).

Fitting facility 304 may be configured to perform one or more of the fitting procedures and/or operations described herein. For example, fitting facility 304 may be configured to define and/or adjust one or more control parameters by which sound processor 104 and/or implantable cochlear stimulator 110 operate, direct sound processor 104 to measure one or more electrode impedances, perform one or more neural response detection operations, and/or perform one or more testing, diagnostic, and/or troubleshooting operations associated with cochlear implant system 100.

Fitting facility 304 may be further configured to direct cochlear implant system 100 to apply electrical stimulation to a patient in accordance with one or more target stimulation levels and/or cochlear implant fitting procedures. For example, fitting facility 304 may be configured to direct cochlear implant system 100 to perform one or more operations of a fitting procedure in accordance with one or more targeted stimulation levels, which may include, without limitation, targeted "M" levels, "T" levels, and/or clipping levels. In certain examples, this may be accomplished by fitting facility 304 providing control parameters to sound processor 104 that are configured to be used by sound processor 104 to direct implantable cochlear stimulator 110 to apply electrical stimulation having certain properties to a patient by way of electrodes 114 on lead 112. For example, stimulation levels of electrical stimulation signals may be controlled by varying electrical properties (e.g., electrical current and/or pulse width) of the electrical stimulation signals in order to adjust the loudness at which the patient perceives sound represented by the electrical stimulation. Different target stimulation levels may be used to apply electrical stimulations to a patient, and patient feedback to the electrical stimulations may be received and considered by a user of fitting subsystem 202 to measure appropriate "M" levels, "T" levels, or other threshold levels to fit cochlear implant system 100 to the patient.

A fitting procedure may include performance any set of one or more fitting operations such as, but not limited to, applying electrical stimulation to a patient to induce a perception of one or more tones when fitting subsystem 202 operates in a "tone burst" operational mode, applying electrical stimulation to a patient in accordance with live audio input received by microphone 102 to induce a perception of the live audio input when fitting subsystem 202 operates in a "live speech" operational mode, and applying electrical stimulation to a patient in accordance with prerecorded audio input to induce a perception of the prerecorded audio input when fitting subsystem 202 operates in a "speech burst" operational mode. Additional or alternative modes of operation may be used in other examples.

User interface facility 306 may be configured to provide one or more user interfaces configured to facilitate user interaction with fitting subsystem 202. For example, user interface facility 306 may provide a GUI through which one or more functions, information, options, features, and/or tools associated with one or more operations described herein may be provided to a user and through which user input may be received. For example, a GUI may provide one or more functions, information, options, features, and/or tools related to one or more fitting procedures. Exemplary views of a fitting GUI including one or more pre-stimulation visual cues displayed therein are described further below. In certain embodiments, user interface facility 306 may be configured to provide the GUI to a display device (e.g., a computer monitor) for display.

Pre-stimulation facility 308 may be configured to determine one or more control parameters to be used by cochlear implant system 100 to apply electrical stimulation to a patient. Pre-stimulation facility 308 may be configured to determine the control parameters in any suitable way. For example, pre-stimulation facility 308 may communicate with any of the other facilities of fitting subsystem 202 to determine the control parameters. Additionally or alternatively, pre-stimulation facility 308 may communicate with sound processor 104 to determine the control parameters. In certain examples, the control parameters may include one or more user-selected target stimulation levels, such as a target "M" level, "T" level, and/or clipping level selected by a user of fitting subsystem 202.

Based on the one or more control parameters, pre-stimulation facility 308 may determine a target stimulation level. The determination may be made in any suitable way. As an example, a target stimulation level included in the control parameters may be set equal to a user-selected "M" level, "T" level, or clipping level that is to be used to apply electrical stimulation to a patient. Pre-stimulation facility 308 may be configured to identify and determine the target stimulation level in the control parameters. Although such an example may involve a straightforward determination, any computation may be performed based on any number of control parameters to determine a target stimulation level. For example, a selected operational mode may be considered by pre-stimulation facility 308 when determining a target stimulation level.

Pre-stimulation facility 308 may be configured to provide data representative of a determined target stimulation level to user interface facility 306 for inclusion in a GUI. Accordingly, as described in more detail further below, user interface facility 306 may display a pre-stimulation visual cue indicative of the determined target stimulation level in a GUI.

Storage facility 310 may be configured to maintain program data 312 representative of one or more sound processing programs, control parameter data 314 representative of one or more control parameters (e.g., one or more user-selected target stimulation levels and/or operational modes), and pre-stimulation data 316 representative of a one or more target stimulation parameters determined by pre-stimulation facility 308. Storage facility 310 may be configured to maintain additional or alternative data as may serve a particular implementation.

Figure 4:
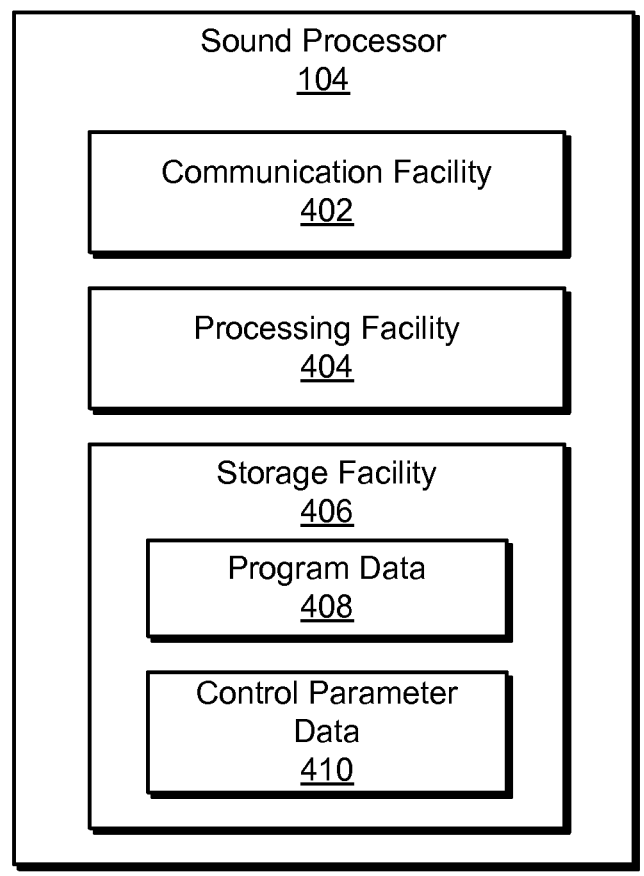
FIG. 4 illustrates exemplary components of a sound processor according to principles described herein.

FIG. 4 illustrates exemplary components of sound processor 104. As shown in FIG. 4, sound processor 104 may include a communication facility 402, a processing facility 404, and a storage facility 406, any or all of which may be in communication with one another using any suitable communication technologies. Each of these facilities will now be described in more detail.

Communication facility 402 may be configured to facilitate communication between sound processor 104 and fitting subsystem 202. For example, communication facility 402 may be configured to facilitate electrical coupling of sound processor 104 to a CPI device in order to communicate with fitting subsystem 202. Communication facility 402 may be further configured to facilitate communication between sound processor 104 and implantable cochlear stimulator 110. For example, communication facility 402 may include transceiver components configured to wirelessly transmit data (e.g., control parameters and/or power signals) to implantable cochlear stimulator 110 and/or wirelessly receive data from implantable cochlear stimulator 110.

Processing facility 404 may be configured to perform one or more signal processing heuristics on an audio signal presented to the patient. For example, processing facility 404 may perform one or more pre-processing operations, spectral analysis operations, noise reduction operations, mapping operations, and/or any other types of signal processing operations on a detected audio signal as may serve a particular implementation. In some examples, processing facility 404 may generate and/or adjust one or more control parameters governing an operation of implantable cochlear stimulator 110 (e.g., one or more stimulation parameters defining the electrical stimulation to be generated and applied by implantable cochlear stimulator 110). Processing facility 404 may be configured to operate in accordance with one or more sound processing programs and/or control parameters loaded onto sound processor 104 by fitting subsystem 202 and/or otherwise stored within storage facility 406.

Storage facility 406 may be configured to maintain program data 408 representative of one or more sound processing programs loaded onto sound processor 104 and control parameter data 410 representative of one or more control parameters. Storage facility 406 may be configured to maintain additional or alternative data as may serve a particular implementation.

Figure 5:
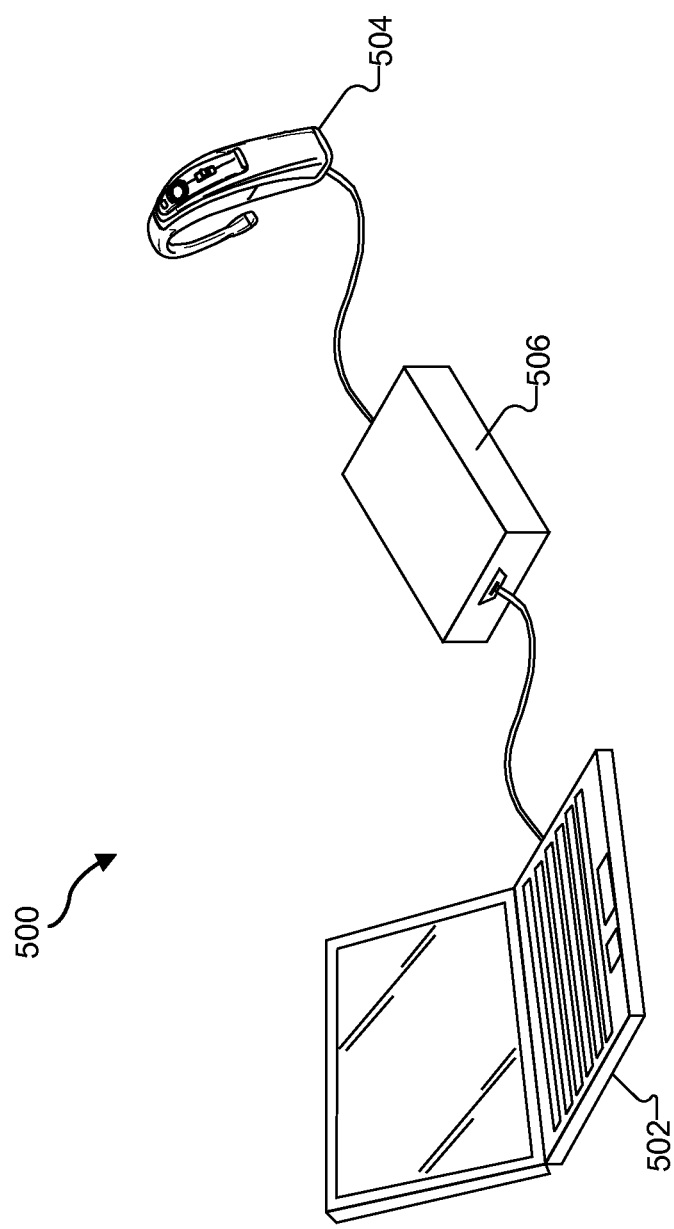
FIG. 5 illustrates an exemplary implementation of the cochlear implant fitting system of FIG. 2 according to principles described herein.

FIG. 5 illustrates an exemplary implementation 500 of fitting system 200. In implementation 500, a fitting station 502 may be selectively and communicatively coupled to a BTE unit 504 by way of a CPI device 506. BTE unit 504 is merely exemplary of the many different types of sound processors that may be used in accordance with the systems and methods described herein. Fitting station 502 may be selectively and communicatively coupled to any other type of sound processor of a cochlear implant system as may serve a particular implementation.

Fitting station 502 may include any suitable computing device and/or combination of computing devices and be configured to perform one or more of the fitting operations described herein. Fitting station 502 may be utilized by an audiologist, a clinician, a product tester, a product manufacturer, and/or any other user to fit BTE unit 504 to a patient.

CPI device 506 may be configured to facilitate communication between fitting station 502 and sound processor 504. In some examples, CPI device 506 may be selectively and communicatively coupled to fitting station 502 and/or BTE unit 504 by way of one or more ports included within fitting station 502 and BTE unit 504.

Figure 6:
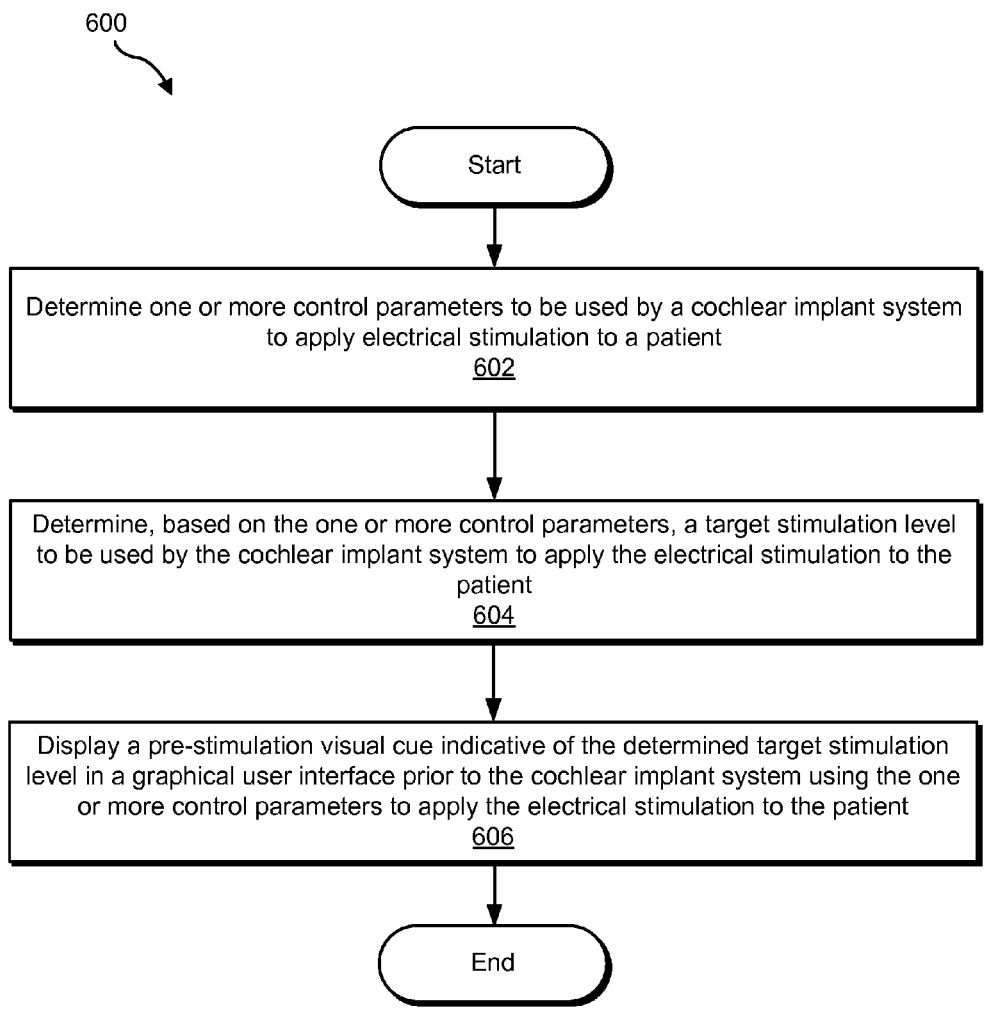
FIG. 6 illustrates an exemplary method of providing a pre-stimulation visual cue representative of a cochlear implant stimulation level according to principles described herein.

FIG. 6 illustrates an exemplary method 600 of providing a pre-stimulation visual cue representative of a cochlear implant stimulation level. While FIG. 6 illustrates exemplary steps according to one embodiment, other embodiments may omit, add to, reorder, combine, and/or modify any of the steps shown in FIG. 6. One or more of the steps shown in FIG. 6 may be performed by any component or combination of components of fitting subsystem 202 and/or fitting station 502.

In step 602, one or more control parameters to be used by a cochlear implant system to apply electrical stimulation to a patient may be determined. For example, fitting subsystem 202 may determine one or more control parameters to be used by cochlear implant system 100 to apply electrical stimulation to a patient in any of the ways described herein.

In step 604, a target stimulation level to be used by the cochlear implant system to apply the electrical stimulation to the patient may be determined based on the one or more control parameters. For example, fitting subsystem 202 may determine, based on the one or more control parameters, a target stimulation level to be used by cochlear implant system 100 to apply the electrical stimulation to the patient. The determination may be made in any of the ways described herein. In certain examples, the determined target stimulation level may represent a target maximum most-comfortable loudness level (i.e., an "M" level), a target minimum threshold level (i.e., a "T" level), or a target maximum clipping level for the electrical stimulation.

In step 606, a pre-stimulation visual cue indicative of the determined target stimulation level may be displayed in a GUI prior to the cochlear implant system using the one or more control parameters to apply the electrical stimulation to the patient. For example, fitting subsystem 202 may display a pre-stimulation visual cue indicative of the determined target stimulation level in a GUI prior to cochlear implant system 100 using the one or more control parameters to apply the electrical stimulation to the patient.

In certain examples, the target stimulation level may be associated with a particular stimulation channel of cochlear implant system 100 (e.g., a stimulation channel associated with a particular electrode on lead 112 of cochlear implant system 100). Accordingly, one or more steps of method 600 may be repeated for each stimulation channel of cochlear implant system 100. For example, step 606 may be repeated to determine, based on one or more control parameters, an additional target stimulation level associated with an additional stimulation channel of cochlear implant system 100, and step 606 may be repeated to display an additional pre-stimulation visual cue indicative of the additional target stimulation level together with the pre-stimulation visual cue in the GUI prior to application of the electrical stimulation to the patient.

Figure 7:
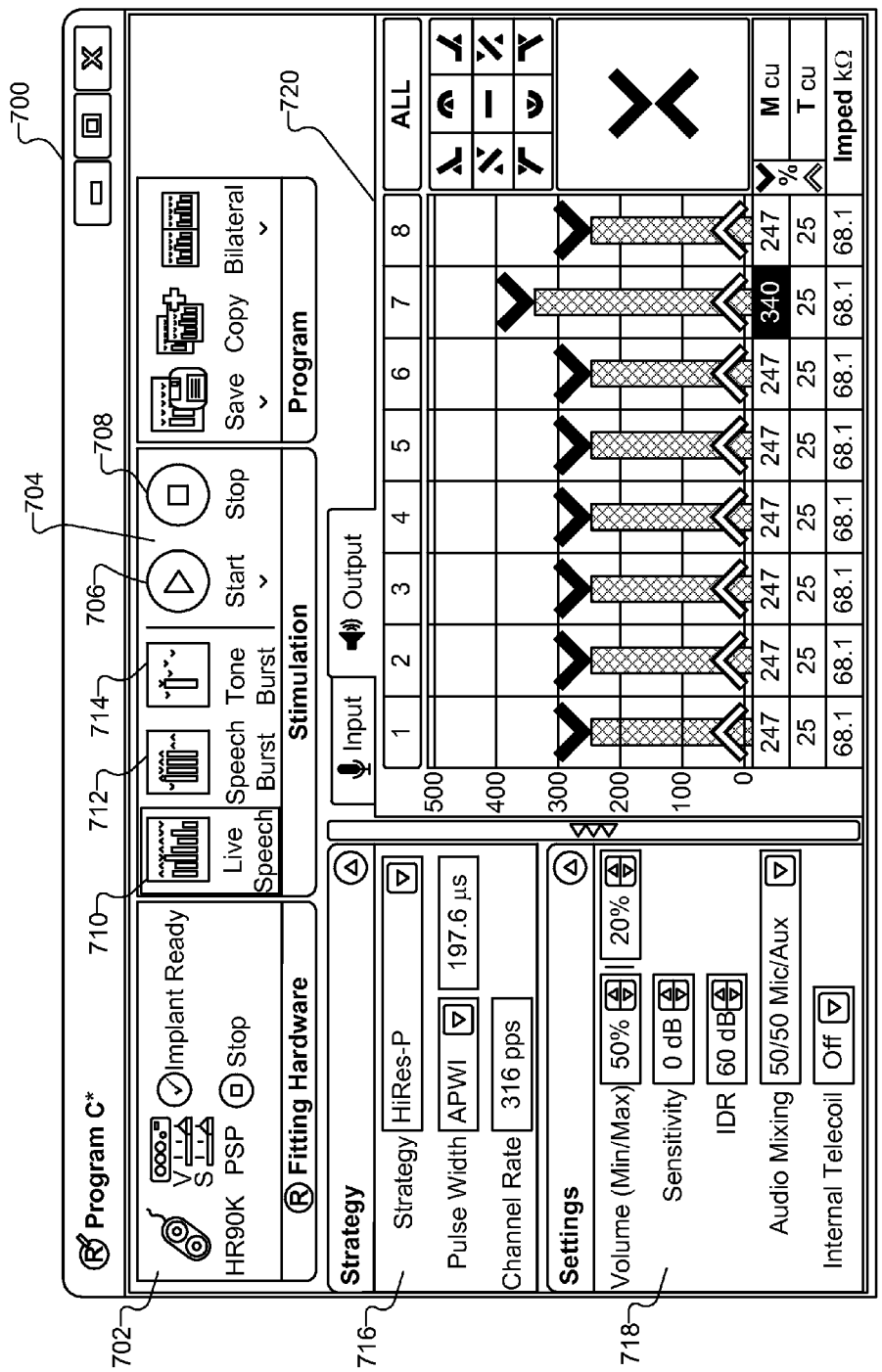
FIGS. 7-9 illustrate exemplary views of a graphical user interface ("GUI") that may be presented for display according to principles described herein.

In step 606, the pre-stimulation visual cue may be displayed in the GUI in any suitable way. For example, FIG. 7 illustrates an exemplary GUI 700 in which one or more pre-stimulation visual cues may be displayed. As shown in FIG. 7, GUI 700 may include a fitting hardware section 702, which may include information about a cochlear implant system (e.g., cochlear implant system 100) that is communicatively coupled to fitting subsystem 202. GUI 700 may also include a stimulation section 704, which may include information and/or user-selectable options associated with configuring, initiating, and stopping application of electrical stimulation to the communicatively coupled cochlear implant system. For instance, stimulation section 704 may include a start option 706 for initiating application of electrical stimulation and a stop option 708 for terminating application of electrical stimulation. Stimulation section 704 may also include a plurality of selectable options associated with a plurality of operational modes of fitting subsystem 202. For example, stimulation section 704 may include a "live speech" option 710, a "speech burst" option 712, and a "tone burst" option 714 respectively associated with a live speech operational mode, a speech burst operational mode, and a tone burst operational mode of fitting subsystem 202. Accordingly, a user may select one of the stimulation operational modes in which fitting subsystem 202 is to operate. In live speech operational mode, live audio input may be captured by microphone 102 and processed by cochlear implant system 100 in accordance with one or more control parameters. In speech burst operational mode, prerecorded audio input may be processed by cochlear implant system 100 in accordance with one or more control parameters. In tone burst operational mode, electrical stimulation representative of one or more specific tones may be applied to a patient by cochlear implant system 100. GUI 700 may also include a strategy section 716 indicating information associated with a selected stimulation strategy (e.g., a sound processing program titled "HiRes-P") and a settings section 718 indicating information associated with one or more settings of a fitting session (e.g., minimum and maximum volume settings).

Figure 8:
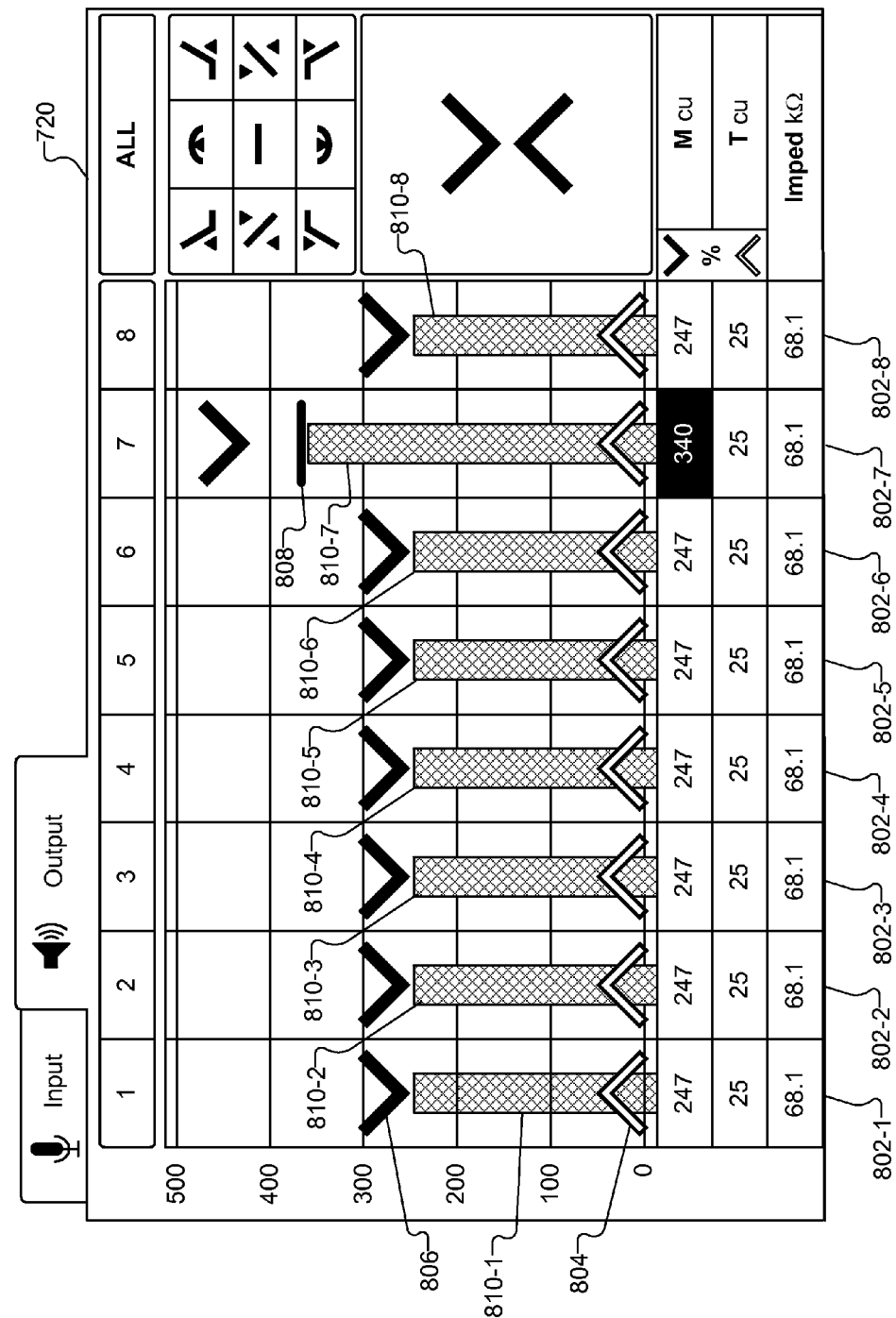

GUI 700 may further include a stimulation chart 720, which may include information and/or options associated with application of electrical stimulation of a patient during a fitting session of a cochlear implant system. An enlarged version of stimulation level chart 720 is illustrated in FIG. 8. As shown in FIG. 8, stimulation level chart 720 may include a plurality of columns 802 (e.g., columns 802-1 through 802-8) associated with a plurality of stimulation channels (e.g., channels 1-8). In certain examples, each stimulation channel may correspond to a particular electrode on lead 112 of cochlear implant system 100. While the exemplary stimulation level chart 720 shown in FIG. 8 includes columns 802-1 through 802-8 representing eight stimulation channels, this is illustrative only. Any number of stimulation channels may be represented in stimulation level chart 720.

Stimulation level chart 720 may include one or more user-controllable graphical objects that may be used by a user to set and/or adjust one or more target stimulation levels to be used to apply electrical stimulation to a patient. In FIG. 8, within each column 802 associated with a stimulation channel, a user-selectable graphical object associated with a "T" level and another user-selectable graphical object associated with an "M" level are displayed. For example, within column 802-1 associated with a first stimulation channel (e.g., channel 1), a "T" level graphical object 804 and an "M" level graphical object 806 are displayed. Objects 804 and 806 may each be user controllable such that a user may select and move each of the objects 804 and 806 independently within column 802-1. By doing so, the user may set a target "T" level and/or a target "M" level for the first stimulation channel. In response to such user input, fitting subsystem 202 may set one or more control parameters equal to the user-selected "T" level and/or "M" level.

Subsequently, fitting subsystem 202 may direct cochlear implant system 100 to apply electrical stimulation to a patient by way of the first stimulation channel in accordance with the control parameters that include the user-selected "T" level and/or "M" level. Through feedback received from the patient, a user of fitting subsystem 202 working together with the patient during a fitting session may determine an appropriate "T" level and/or "M" level for the patient. To illustrate, a user may move "M" level graphical object 806 to a particular target stimulation level (which may be measured in terms of "clinical units," a unit that may be a function of electrical current, a combination of electrical current and pulse width, or any other electrical property or combination of electrical properties that may affect perceived loudness caused by electrical stimulation) within stimulation level chart 720 to set a target "M" level for the first channel. Accordingly, a subsequent application of electrical stimulation to a patient by way of the first channel may be based at least in part on the user-selected target "M" level. For example, one or more properties (e.g., an electrical current value and/or a pulse width) of the electrical stimulation may be determined and applied based on the user-selected target "M" level.

While objects 804 and 806 have been described within a context of a single stimulation channel, this is illustrative only. Each stimulation channel represented in GUI 700 may be similarly associated with one or more user-selectable graphical objects that may be utilized by a user to set target stimulation levels. Accordingly, a user may utilize one or more user-selectable graphical objects in GUI 700 to set one or more target stimulation levels that are to be used by cochlear implant system 100 to apply electrical stimulation to a patient for the purpose of measuring appropriate "T" levels and/or "M" levels for the patient.

In addition or alternative to stimulation level chart 720 including graphical objects that may be used to set "T" levels and/or "M" levels to be used in application of electrical stimulation to a patient, stimulation level chart 720 may include other user-controllable graphical objects that may be similarly used to set target stimulation levels to be used in application of electrical stimulation to the patient. For example, FIG. 8 illustrates a clipping graphical object 808 that may be controlled by a user to set a maximum level at which electrical stimulation will be clipped. In the example shown in FIG. 8, graphical object 808 is positioned such that a stimulation level will be clipped below a set "M" level for a seventh electrical stimulation channel of cochlear implant system 100. While graphical object 808 visually indicates that the stimulation level associated with the seventh stimulation channel will be clipped, a clipping level may be enabled without visual indication in GUI 700. As used herein, the term "clipping" may include any limiting of a stimulation level to a certain threshold. The limiting may be accomplished in any suitable way, including by limiting (e.g., distorting) an electrical current level, a pulse width, and/or any other electrical property (e.g., amplitude, frequency, etc.) that affects the stimulation level. Clipping may be enabled automatically by one or more fitting operations performed by fitting subsystem 202, in response to user input (e.g., user placement of clipping graphical object 808 in GUI 700), and/or based on any attributes (e.g., signal processing limitations) of fitting subsystem 202 and/or cochlear implant system 100.

While the above-described user-controllable graphical objects are generally useful for setting and adjusting target stimulation levels for application of electrical stimulation to a patient, target stimulation levels may not always be intuitive to a user of fitting subsystem 202 based only on the user-controllable graphical objects. For example, a user may not recall which user-configurable graphical object was most recently selected, or the user may not be aware of a particular control parameter that will affect target stimulation levels. For example, a stimulation level associated with a stimulation channel may be set to be clipped (e.g., below an "M" level and/or a "T" level) without any visual indication in GUI 700 that clipping is enabled or that the stimulation level is to be clipped. For example, a particular operational mode may automatically enable clipping without providing any visual indication of the clipping before electrical stimulation is applied. For instance, clipping of a stimulation level associated with a seventh stimulation channel ("channel 7") may be enabled, but clipping graphical object 808 may be omitted from GUI 700. Accordingly, the clipping may not be intuitively discerned by a user of fitting subsystem 202.

As mentioned, GUI 700 may include one or more pre-stimulation visual cues displayed therein. The pre-stimulation visual cues, which may be displayed prior to application of electrical stimulation associated with the pre-stimulation visual cues to a patient, may provide an intuitive indication of target stimulation levels that are to be used in electrical stimulation of the patient. For example, FIG. 8 illustrates a plurality of pre-stimulation visual cues 810 (e.g., pre-stimulation visual cues 810-1 through 810-8) displayed prior to application of associated electrical stimulation to a patient. As shown, each of the pre-stimulation visual cues 810 corresponds to a particular stimulation channel. For instance, pre-stimulation visual cue 810-1 corresponds to a first stimulation channel associated with column 802-1 in stimulation level chart 720.

As mentioned, pre-stimulation visual cues 810 are indicative of determined target stimulation levels to be used in application of electrical stimulation to a patient. Pre-stimulation visual cues 810 may be indicative of target stimulation levels in that one or more properties of electrical stimulation signals applied to a patient may be determined based on the target stimulation levels. Actual stimulation levels used to apply electrical stimulation to the patient may correspond to or vary from the target stimulation levels depending on one or more other factors, such as actual loudness of a captured sound that is used as input to a fitting procedure.

In certain examples, pre-stimulation visual cues 810 may represent maximum stimulation levels to be used in application of electrical stimulation to the patient. For instance, pre-stimulation visual cue 810-7 represents a maximum stimulation level at which electrical stimulation will be clipped in accordance with clipping graphical object 808. The other pre-stimulation visual cues 810-1 through 810-6 and 810-8 represent maximum most-comfortable stimulation levels that correspond to "M" levels that have been set for use in application of electrical stimulation to the patient.

Pre-stimulation visual cues may be displayed together with one or more user-controllable graphical objects such as graphical objects 804, 806, and 808 in GUI 700 as shown in FIG. 8. This may provide a highly intuitive indication of target stimulation levels to a user.

In the example illustrated in FIG. 8, pre-stimulation visual cues 810 may include vertical bar graphical objects positioned with respective columns 802. The height of a vertical bar within stimulation level chart 720 may graphically depict a target stimulation level (e.g., a value in terms of clinical units ("cu")). In certain embodiments, pre-stimulation visual cues 810 may be semi-transparent, which may be designed to indicate that the pre-stimulation visual cues 801 are precursors of target stimulation levels associated with electrical stimulations that have not yet been applied to a patient.

Fitting subsystem 202 may be configured to display pre-stimulation visual cues 810 in response to any predetermined event. For example, pre-stimulation visual cues 810 may be displayed in response to receipt of a predetermined user input or automatically in response to a launch of GUI 700. In certain examples, pre-stimulation visual cues 810 may be dynamically updated in GUI 700 as control parameters are updated, such as when a user utilizes a user-controllable graphical object to set a target stimulation level such as an "M" level, "T" level, or clipping level.

With control parameters selected as shown in FIGS. 7 and 8, a user of fitting subsystem 202 may select start option 706 to initiate application of the electrical stimulation to a patient. In response, fitting subsystem 202 may direct cochlear implant system 100 to apply the electrical stimulation to the patient in accordance with the control parameters. During application of the electrical stimulation to the patient, one or more actual stimulation levels associated with the application of the electrical stimulation may be depicted in GUI 700. For example, FIG. 9 illustrates stimulation level chart 720 having one or more stimulation visual cues 910 (e.g., stimulation visual cues 910-1 through 910-8) indicative of actual stimulation levels at which cochlear implant system 100 applies the electrical stimulation to the patient in accordance with the control parameters.

Figure 9:
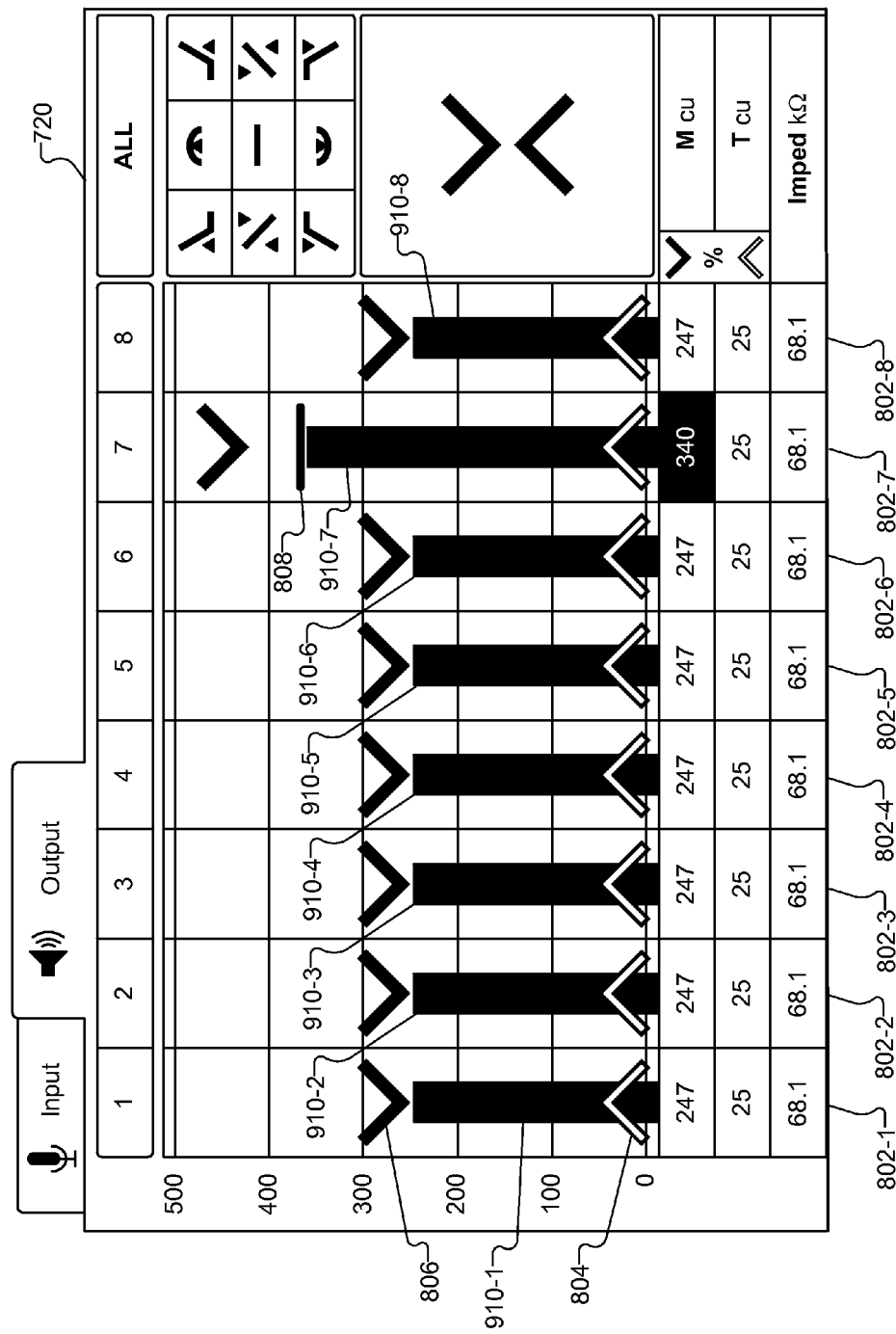

As shown in FIG. 9, stimulation visual cues 910 may include opaque vertical bar graphical objects within stimulation level chart 720 in GUI 700. In certain embodiments, during application of the electrical stimulation to the patient, pre-stimulation visual cues 810 may continue to be displayed in GUI 700, and stimulation visual cues 910 may overlay pre-stimulation visual cues 810. In some examples, such as the example illustrated in FIG. 9, target stimulation levels and actual stimulation levels may be equivalent, and pre-stimulation visual cues 810 and stimulation visual cues 910 may indicate the equivalence. For example, a vertical bar representing an actual stimulation level and a vertical bar representing a target stimulation level may be substantially equivalent in size to graphically depict an equivalence of the target stimulation level and the actual stimulation level. Conversely, a difference in a target stimulation level and an actual stimulation level may be graphically depicted by a difference in the sizes of a vertical bar representing the actual stimulation level and a vertical bar representing the target stimulation level.

While FIGS. 7-9 illustrate certain exemplary graphical representations of visual cues according to principles described herein, the examples are illustrative only. Other graphical representations of visual cues may be used in other implementations.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 10:
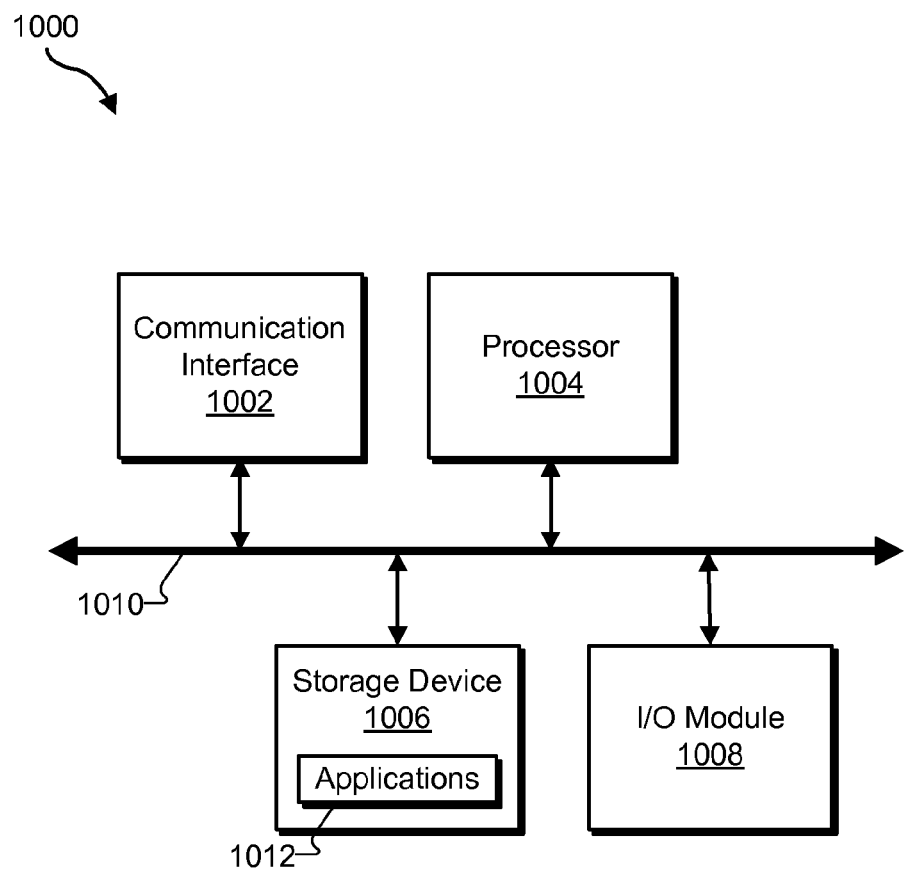
FIG. 10 illustrates an exemplary computing device according to principles described herein.

FIG. 10 illustrates an exemplary computing device 1000 that may be configured to perform one or more of the processes described herein. As shown in FIG. 10, computing device 1000 may include a communication interface 1002, a processor 1004, a storage device 1006, and an input/output ("I/O") module 1008 communicatively connected via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, and any other suitable interface. Communication interface 1002 may additionally or alternatively provide such a connection through, for example, a local area network (such as an Ethernet network), a personal area network, a telephone or cable network, a satellite data connection, a dedicated URL, or any other suitable connection. Communication interface 1002 may be configured to interface with any suitable communication media, protocols, and formats, including any of those mentioned above.

Processor 1004 generally represents any type or form of processing unit capable of processing data or interpreting, executing, and/or directing execution of one or more of the instructions, processes, and/or operations described herein. Processor 1004 may direct execution of operations in accordance with one or more applications 1012 or other computer-executable instructions such as may be stored in storage device 1006 or another non-transitory computer-readable medium.

Storage device 1006 may include one or more data storage media, devices, or configurations and may employ any type, form, and combination of data storage media and/or device. For example, storage device 1006 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1006. For example, data representative of one or more executable applications 1012 (which may include, but are not limited to, one or more of the software applications described herein) configured to direct processor 1004 to perform any of the operations described herein may be stored within storage device 1006. In some examples, data may be arranged in one or more databases residing within storage device 1006.

I/O module 1008 may be configured to receive user input and provide user output and may include any hardware, firmware, software, or combination thereof supportive of input and output capabilities. For example, I/O module 1008 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1008 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1000. For example, one or more applications 1012 residing within storage device 1006 may be configured to direct processor 1004 to perform one or more processes or functions associated with communication facility 302, fitting facility 304, user interface facility 306, pre-stimulation facility 308, communication facility 402, and/or processing facility 404. Likewise, storage facility 310 and/or storage facility 406 may be implemented by or within storage device 1006.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   at least one computing device communicatively coupled to a cochlear implant system and that:
   determines one or more control parameters to be used by the cochlear implant system to apply electrical stimulation to a patient,
   determines, based on the one or more control parameters, a target stimulation level to be used by the cochlear implant system to apply the electrical stimulation to the patient, and
   displays a pre-stimulation visual cue indicative of the determined target stimulation level in a graphical user interface prior to the cochlear implant system using the one or more control parameters to apply the electrical stimulation to the patient.

2. The system of claim 1, wherein the determined target stimulation level represents a most-comfortable loudness level for the electrical stimulation.

3. The system of claim 1, wherein the determined target stimulation level is associated with a stimulation channel of the cochlear implant system.

4. The system of claim 1, wherein the at least one computing device:
   determines an additional target stimulation level based on the one or more control parameters; and
   displays an additional pre-stimulation visual cue indicative of the determined additional target stimulation level together with the pre-stimulation visual cue in the graphical user interface prior to the cochlear implant system using the one or more control parameters to apply the stimulation to the patient;
   wherein the target stimulation level is associated with a stimulation channel of the cochlear implant system and the additional target stimulation level is associated with an additional stimulation channel of the cochlear implant system.

5. The system of claim 1, wherein the one or more control parameters comprise at least one of a most-comfortable level, a threshold level, and a clipping level.

6. The system of claim 1, wherein the one or more control parameters comprise an operational mode of the at least one computing device.

7. The system of claim 6, wherein the operational mode of the at least one computing device comprises one of a live speech mode, a speech burst mode, and a tone burst mode of the at least one computing device.

8. The system of claim 1, wherein the pre-stimulation visual cue comprises a vertical bar graphical object within a stimulation level chart in the graphical user interface.

9. The system of claim 8, wherein the vertical bar graphical object is semi-transparent.

10. The system of claim 1, wherein the at least one computing device:
    receives a user input command to apply the electrical stimulation to the patient;

directs the cochlear implant system to apply the electrical stimulation to the patient in accordance with the one or more control parameters; and displays, in the graphical user interface, a stimulation visual cue indicative of an actual stimulation level at which the cochlear implant system applies the electrical stimulation to the patient in accordance with the one or more control parameters.

11. The system of claim 10, wherein:

the pre-stimulation visual cue comprises a semi-transparent vertical bar graphical object within a stimulation level chart in the graphical user interface; and the stimulation visual cue comprises an opaque vertical bar graphical object within the stimulation level chart in the graphical user interface.

12. The system of claim 11, wherein the opaque vertical bar graphical object overlays the semi-transparent vertical bar graphical object in the graphical user interface during the application of the electrical stimulation to the patient.

13. The system of claim 11, wherein:

the determined target stimulation level and the actual stimulation level are equivalent; and the semi-transparent vertical bar graphical object and the opaque vertical bar graphical object graphically indicate the equivalence.

14. A system comprising:

at least one computing device that:

determines, based on one or more control parameters, a target stimulation level to be used by a cochlear implant system communicatively coupled to the at least one computing device to apply electrical stimulation to a patient in accordance with a cochlear implant fitting procedure; and displays a pre-stimulation visual cue indicative of the determined target stimulation level in a stimulation chart in a graphical user interface prior to the cochlear implant system using the one or more control parameters to apply the electrical stimulation to the patient in accordance with the cochlear implant fitting procedure.

15. The system of claim 14, wherein the at least one computing device:

receives a user input command to initiate an actual application of the electrical stimulation to the patient;

executes, in response to the user input command, the cochlear implant fitting procedure to direct the cochlear implant system to apply the electrical stimulation to the cochlea of the patient based on the one or more control parameters; and displays, in the graphical user interface, a stimulation visual cue indicative of an actual stimulation level at which the cochlear implant system applies the electrical stimulation to the patient based on the one or more control parameters.

16. The system of claim 15, wherein:

the pre-stimulation visual cue comprises a semi-transparent vertical bar graphical object within the stimulation level chart in the graphical user interface; and the stimulation visual cue comprises an opaque vertical bar graphical object overlaying the semi-transparent vertical bar graphical object within the stimulation level chart in the graphical user interface.

17. The system of claim 14, wherein the at least one computing device:

displays at least one of a user-controllable most-comfortable loudness level graphical object, a user-controllable threshold loudness level graphical object, and a user-controllable clipping loudness level graphical object together with the pre-stimulation visual cue in the stimulation chart in the graphical user interface.

18. A system comprising:

a communication facility communicatively coupled to a cochlear implant system;

a fitting facility communicatively coupled to the communication facility and configured to direct the cochlear implant system to apply electrical stimulation to a patient in accordance with a cochlear implant fitting procedure;

a pre-stimulation facility communicatively coupled to at least one of the communication facility and the fitting facility and configured to determine one or more control parameters to be used by the cochlear implant system to apply the electrical stimulation to the patient in accordance with the cochlear implant fitting procedure, and determine a target stimulation level based on the one or more control parameters; and a user interface facility communicatively coupled to the pre-stimulation facility and configured to display a pre-stimulation visual cue indicative of the determined target stimulation level in a graphical user interface prior to the fitting facility directing the cochlear implant system to apply the electrical stimulation to the patient in accordance with the cochlear implant fitting procedure.

19. The system of claim 18, wherein the determined target stimulation level represents a most-comfortable loudness level for the electrical stimulation.

20. The system of claim 18, wherein the determined target stimulation level is associated with a stimulation channel of the cochlear implant system.

* * * * *